United States Patent
Shinomiya et al.

(10) Patent No.: US 7,972,246 B2
(45) Date of Patent: Jul. 5, 2011

(54) WALKING ABILITY DIAGNOSIS SYSTEM

(75) Inventors: Youichi Shinomiya, Ibaraki (JP); Kazuhiro Ochi, Osaka (JP); Takahisa Ozawa, Katano (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 25 days.

(21) Appl. No.: 12/525,041

(22) PCT Filed: Jan. 30, 2007

(86) PCT No.: PCT/JP2007/051511
§ 371 (c)(1),
(2), (4) Date: Jul. 29, 2009

(87) PCT Pub. No.: WO2008/093406
PCT Pub. Date: Aug. 7, 2008

(65) Prior Publication Data
US 2010/0035728 A1    Feb. 11, 2010

(51) Int. Cl.
*A63B 71/00* (2006.01)
(52) U.S. Cl. .............. 482/8; 482/1; 482/51; 482/54; 482/901; 600/595
(58) Field of Classification Search ............ 482/1–9, 482/51, 54, 74, 900–902; 434/247; 601/23, 601/27–35; 600/595
See application file for complete search history.

(56) References Cited

U.S. PATENT DOCUMENTS

| | | | |
|---|---|---|---|
| 5,207,621 A * | 5/1993 | Koch et al. | 482/53 |
| 6,231,527 B1 | 5/2001 | Sol | |
| 6,632,158 B1 | 10/2003 | Nashner | |
| 6,645,126 B1 | 11/2003 | Martin et al. | |
| 7,822,472 B1 * | 10/2010 | Xi | 600/519 |
| 2002/0130951 A1 * | 9/2002 | Kurono | |
| 2004/0059264 A1 | 3/2004 | Nishibe et al. | |
| 2006/0058704 A1 | 3/2006 | Graichen et al. | |
| 2006/0251334 A1 * | 11/2006 | Oba et al. | 382/275 |
| 2008/0082025 A1 * | 4/2008 | Hughes et al. | 600/595 |
| 2008/0214963 A1 * | 9/2008 | Guillemaud et al. | 600/595 |
| 2009/0254004 A1 | 10/2009 | Graichen et al. | |

FOREIGN PATENT DOCUMENTS

| | | | |
|---|---|---|---|
| EP | 1 145 682 A2 | | 10/2001 |
| JP | 9-168529 A | * | 6/1997 |
| JP | 9-276348 A | * | 10/1997 |
| JP | 10-248889 A | | 9/1998 |

(Continued)

OTHER PUBLICATIONS

Notification of Reasons for Refusal for the Application No. 2005-227108 from Japan Patent Office mailed Jan. 12, 2010.

(Continued)

*Primary Examiner* — Glenn Richman
(74) *Attorney, Agent, or Firm* — Cheng Law Group, PLLC

(57) ABSTRACT

A sensor unit installed in a premises for detecting a user's walking behavior. Connected to the server through a communication network are a server, an information reporting unit, and an exercise machine. The server includes a diagnosis section for analyzing time series data of walking signal from the sensor unit to determine walking ability and generate walking ability data indicative thereof, and an information providing section which provides the walking ability date to the information reporting unit and the exercise machine. The information reporting unit includes reporting means for reporting the determined walking ability to the user. The exercise machine includes a control section which gives an exercise to the user depending upon the walking ability.

22 Claims, 13 Drawing Sheets

FOREIGN PATENT DOCUMENTS

| | | | | |
|---|---|---|---|---|
| JP | 11-9378 | A | | 1/1999 |
| JP | 2000-300694 | A | | 10/2000 |
| JP | 2002-277213 | A | * | 9/2002 |
| JP | 2002-345785 | A | * | 12/2002 |
| JP | 2003-204953 | A | * | 7/2003 |
| JP | 2003-310577 | A | * | 11/2003 |
| JP | 2005-160747 | A | * | 6/2005 |
| JP | 2005-168907 | A | | 6/2005 |
| JP | 2006-218202 | A | * | 8/2006 |
| JP | 2007-37852 | A | * | 2/2007 |

OTHER PUBLICATIONS

International Search Report for the Application No. PCT/JP2007/051511 mailed Feb. 27, 2007.*

Notification of Reasons for Refusal for the Application No. 2005-227108 from Japan Patent Office mailed Sep. 1, 2009.

Supplementary European Search Report for the Application No. EP 07 70 7729 dated Mar. 22, 2011.

* cited by examiner

FIG. 2
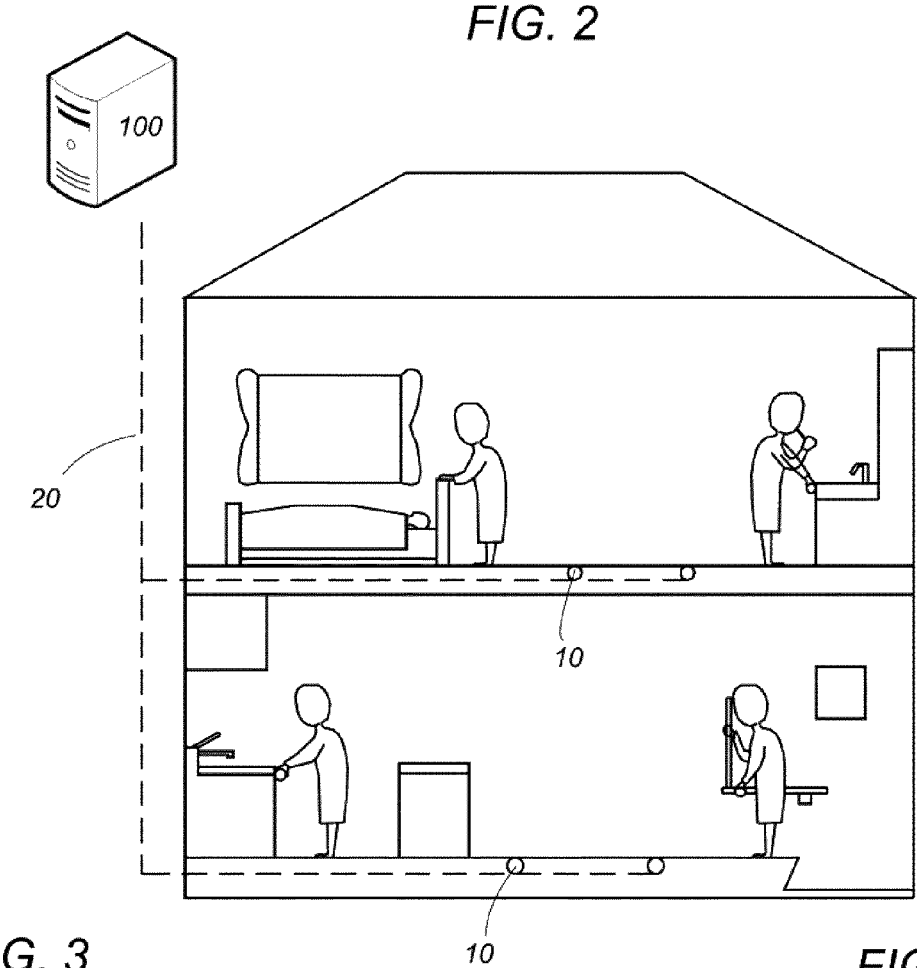
FIG. 3
FIG. 4
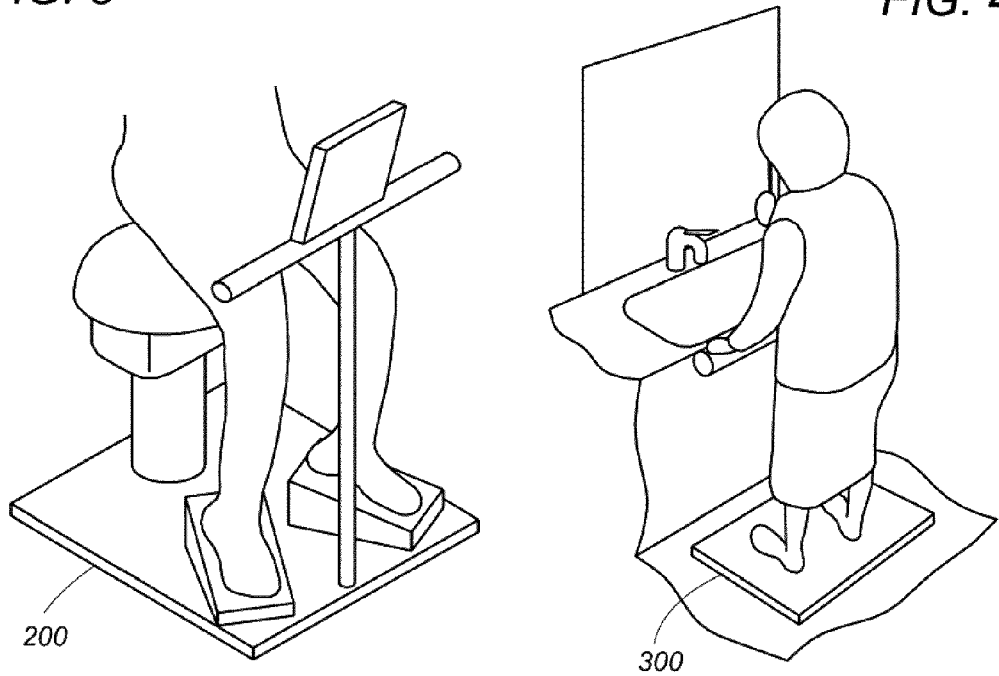

FIG. 14
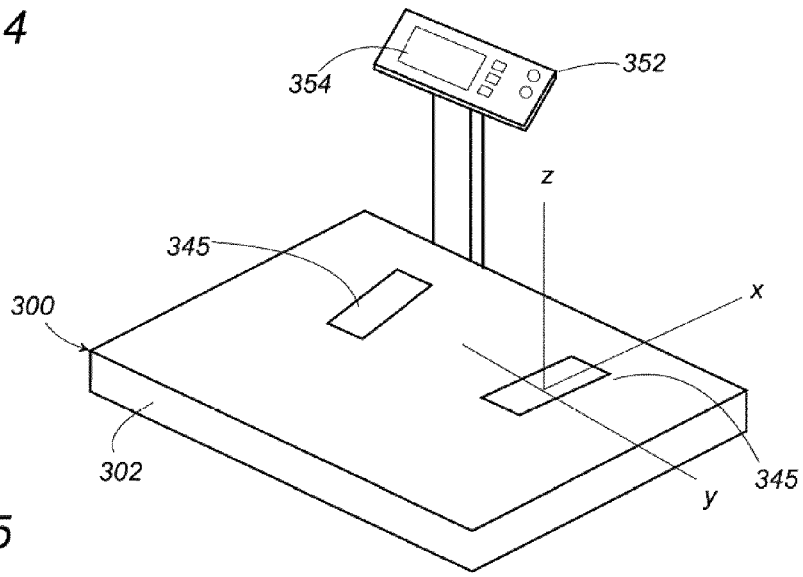
FIG. 15
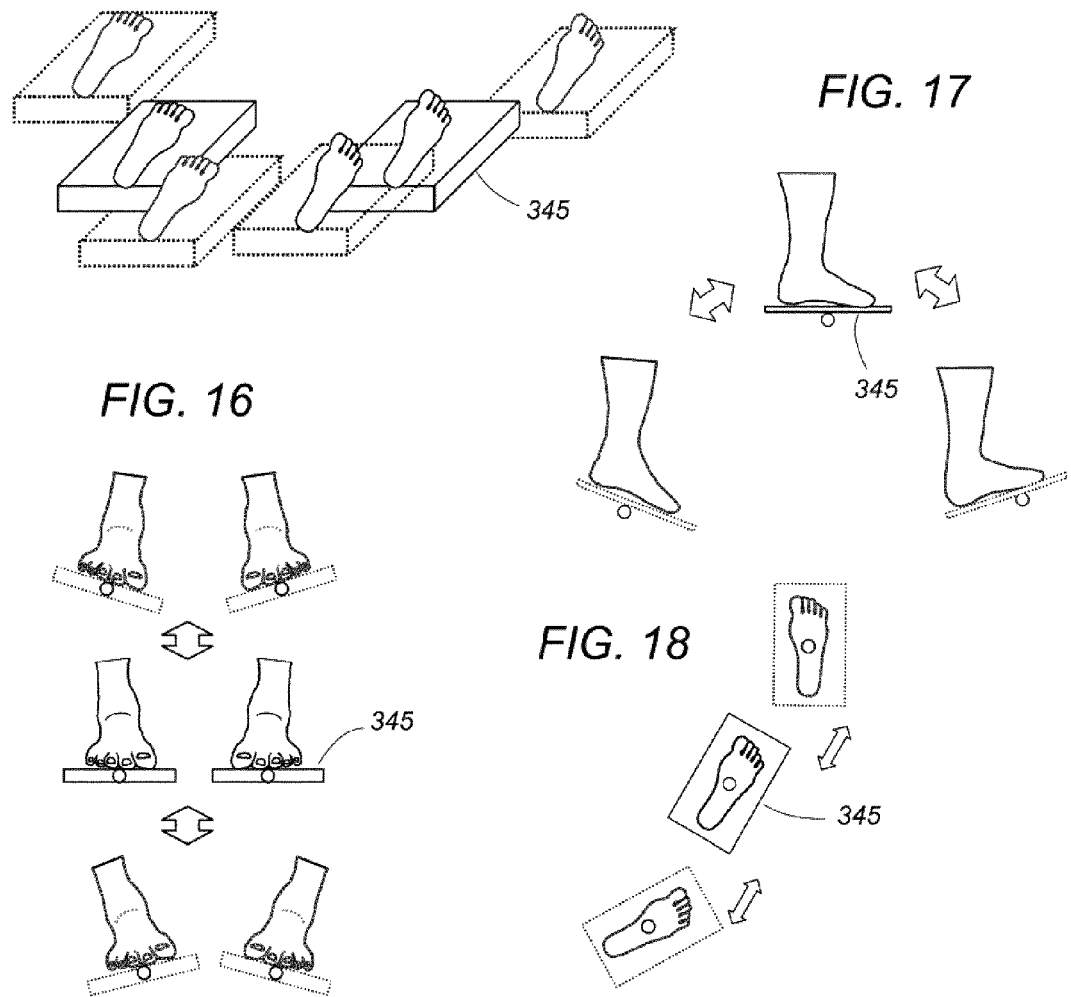
FIG. 17
FIG. 16
FIG. 18

FIG. 19

Measurement data

| Data acquisition time | L- foot touching time (sec) | R-foot touching time (sec) |
|---|---|---|
| t00 | 0.6 | 0.5 |
| t01 | 0.6 | 0.5 |
| t02 | 0.6 | 0.4 |
| t03 | 0.6 | 0.5 |
| t04 | 0.6 | 0.4 |
| t04 | 0.6 | 0.5 |
| t06 | 0.6 | 0.5 |
| t07 | 0.6 | 0.4 |
| t08 | 0.6 | 0.5 |
|  |  |  |

FIG. 20

User table

| User code | Name | Age | Sex | Height | Face judgment data | Update time |
|---|---|---|---|---|---|---|
| 001 | AAA | 53 | male | 171 | 01001 | 2006.01.01.12:00:10 |
| 002 | BBB | 62 | female | 155 | 01000 | 2006.01.01.12:00:20 |
| 003 | CCC | 60 | male | 162 | 01010 | 2006.01.01.12:10:10 |
| 004 | DDD | 72 | female | 158 | 01101 | 2006.01.01.12:10:30 |
|  |  |  |  |  |  |  |
|  |  |  |  |  |  |  |
|  |  |  |  |  |  |  |

FIG. 21

Judgment table

| Judgment time | Leg strength | Leg balance ratio | User code | Exercise project | Exercise machine |
|---|---|---|---|---|---|
| T001 | 09 | +106 | 001 | 09+106-171-X | 01 |
| T002 | 05 | -110 | 002 | 05-110-155-Y | 01 |
| T003 |  |  |  |  |  |
| T004 |  |  |  |  |  |
| T005 |  |  |  |  |  |
| T006 |  |  |  |  |  |
| T007 |  |  |  |  |  |

*FIG. 22*

History view of users' judgment data

| User | Leg strength | Leg balance ratio | Exercise project | Exercise machine | Update time |
|---|---|---|---|---|---|
| 001 | 09 | +110 | 09+110-171-X | 01 | 2005.12.31.12:00:10 |
| 001 | 09 | +106 | 09+106-171-X | 01 | 2006.01.01.12:00:10 |
| 002 | 04 | -112 | 05-112-155-Y | 01 | 2005.12.31.12:10:20 |
| 002 | 04 | -110 | 05-110-155-Y | 01 | 2006.01.01.12:10:30 |
| 003 |  |  |  |  |  |
|  |  |  |  |  |  |
|  |  |  |  |  |  |

*FIG. 23*

Leg strength conversion table

| Leg strength | Floor-contact time | Load (kg.f) | Foot step |
|---|---|---|---|
| 01 | < 0.3 | < 30 | < 20 |
| 02 | 0.30-0.34 | 30-34 | 20-24 |
| 03 | 0.35-0.39 | 35-39 | 25-29 |
| 04 | 0.40-0.44 | 40-44 | 30-34 |
| 05 | 0.45-0.49 | 45-49 | 35-39 |
| 06 | 0.50-0.54 | 50-54 | 40-44 |
| 07 | 0.55-0.59 | 55-59 | 45-49 |
| 08 | 0.60-0.64 | 60-64 | 50-54 |
| 09 | 0.65-0.69 | 65-69 | 55-59 |
| 10 | 0.70-0.74 | 70-74 | 60-64 |
| 11 | 0.75-0.79 | 75-79 | 65-69 |
| 12 | 0.80-0.89 | 80-84 | 70-79 |
| 13 | 0.90-1.00 | 85-89 | 80-89 |
| 14 | 1.0 < | 90 < | 90 < |

FIG. 24

Exercise project parameters

| Leg strength | Reference leg | Leg balance ratio | Height (cm) | BMI | sex |
|---|---|---|---|---|---|
| 009 | R | 106 | 172 | 24 | X |
| 007 | L | 110 | 162 | 21 | Y |
| | | | | | |

FIG. 25

Exercise machine table

| Exercise machine code | Leg balance improvement | Exercise level | Applicable age | Applicable BMI |
|---|---|---|---|---|
| 01 | Y | 100 | 15 < | < 35 |
| 02 | N | 85 | 15-80 | > 18 |
| 03 | Y | 50 | ALL | ALL |
| | | | | |
| | | | | |

FIG. 26

Exercise control table

| Leg strength | Knee angle (°) | Exercise angle range θ | Movement cycle | Time (sec) |
|---|---|---|---|---|
| 01 | 170 | 4.5 | 1.0 | 5 |
| 02 | 165 | 5.0 | 1.2 | 5 |
| 03 | 165 | 5.0 | 1.2 | 6 |
| 04 | 160 | 5.5 | 1.2 | 6 |
| 05 | 160 | 5.5 | 1.3 | 7 |
| 06 | 155 | 6.0 | 1.3 | 7 |
| 07 | 155 | 6.0 | 1.3 | 8 |
| 08 | 150 | 6.5 | 1.4 | 9 |
| 09 | 150 | 6.5 | 1.4 | 10 |
| 10 | 145 | 7.0 | 1.4 | 11 |
| 11 | 145 | 7.0 | 1.5 | 12 |
| 12 | 140 | 7.5 | 1.5 | 13 |
| 13 | 140 | 7.5 | 1.6 | 14 |
| 14 | 135 | 8 | 1.6 | 15 |

| Data acquisition time | L-foot step (cm) | R-foot step (cm) |
|---|---|---|
| t00 | 45 | 42 |
| t01 | 45 | 43 |
| t02 | 44 | 43 |
| t03 | 45 | 43 |
| t04 | 44 | 42 |
| t04 | 45 | 43 |
| t06 | 45 | 43 |
| t07 | 45 | 42 |
| t08 | 45 | 43 |
|  |  |  |

Measurement data

| Measurement data | | | | |
|---|---|---|---|---|
| Data acquisition time | L | R | L-pressure Mpa | R-pressure Mpa |
| t00 | 17.2 | 15.8 | 9.4 | 8.6 |
| t01 | 17.1 | 16.0 | 9.3 | 8.7 |
| t02 | 17.1 | 16.0 | 9.4 | 8.6 |
| t03 | 17.0 | 16.1 | 9.4 | 8.6 |
| t04 | 17.1 | 15.9 | 9.3 | 8.7 |
| t04 | 17.2 | 15.8 | 9.3 | 8.7 |
| t06 | 17.1 | 16.0 | 9.3 | 8.7 |
| t07 | 17.1 | 15.9 | 9.4 | 8.6 |
| t08 | 17.1 | 15.9 | 9.3 | 8.7 |
| | | | | |

| Measurement data | | | | |
|---|---|---|---|---|
| Data acquisition time | L-pressure Mpa | R-pressure Mpa | L-offset distance (cm) | R-offset distance (cm) |
| t00 | 9.4 | 8.6 | 17.2 | 15.8 |
| t01 | 9.3 | 8.7 | 17.1 | 16.0 |
| t02 | 9.4 | 8.6 | 17.1 | 16.0 |
| t03 | 9.4 | 8.6 | 17.0 | 16.1 |
| t04 | 9.3 | 8.7 | 17.1 | 15.9 |
| t04 | 9.3 | 8.7 | 17.2 | 15.8 |
| t06 | 9.3 | 8.7 | 17.1 | 16.0 |
| t07 | 9.4 | 8.6 | 17.1 | 15.9 |
| t08 | 9.3 | 8.7 | 17.1 | 15.9 |

| Data acquisition time | Floor load (kg) | Handrail load (Kg) | Left/Right |
|---|---|---|---|
| t00 | 55 | 10 | L |
| t01 | 56 | 9 | R |
| t02 | 55 | 10 | L |
| t03 | 56 | 9 | R |
| t04 | 55 | 10 | L |
| t04 | 56 | 9 | R |
| t06 | 55 | 10 | L |
| t07 | 56 | 9 | R |
| t08 | 56 | 9 | L |

Measurement data

WALKING ABILITY DIAGNOSIS SYSTEM

TECHNICAL FIELD

The present invention relates to a walking ability diagnosis system for determining a user's walking ability based on a routine activity of a user.

BACKGROUND ART

Japanese Patent Publication No. 9-168529 discloses a device for measurement of foot step, waking speed, weight shifting of a user in walking. The device can be used to analyze the walking behavior to determine the user's walking ability. However, the device requires the user to walk on a mat equipped in the device, and is difficult to closely reproduce routing activity of the user. Therefore, the device suffers from a shortcoming of not able to measure the physical ability required on a basis of routine activity. As it is required especially for elders to examine the physical ability based on the routine activity, a system is demanded to realize such requirement.

DISCLOSURE OF THE INVENTION

The present invention has been achieved in view of the above problem to provide a walking ability diagnosis system which is capable of determining user's physical ability based on a routine activity and report the same to the user.

The walking ability diagnosis system in accordance with the present invention includes a sensor unit installed in a premises and configured to measure walking behavior of a user, a server connected to the sensor unit by way of a communication network provided in said premises, and an information reporting unit connected to the server by way of said communication network. The sensor unit is configured to output a walking signal indicative of a user's walking behavior. The server includes a sensor information processing section configured to store time series data of the walking signal transmitted from the sensor unit, a diagnosis section configured to analyze the time series data to determine the walking ability and generate walking ability data indicative of the walking ability; and an information providing section configured to transmit a selected one of the walking ability data to the communication network. The information reporting unit includes reporting means for providing the selected walking ability data to the user. With this arrangement, it is possible to determine the walking ability of the user on a basis of the user's routine activity within the premises. Further, since the output of the sensor unit is transmitted to the server through the communication network, the sensor unit can be installed at a location remote from the server, which enhances installation flexibility and enables the installation in well dependence upon internal structure of the premises. Especially, the sensor unit is allowed to be installed at a variety of position for accurately measuring the user's routine activity.

The server is preferred to have a judgment table. In this connection, the diagnosis section is configured to analyze a leg strength based upon the time series data within a predetermined time range and judge the same as the walking ability data, and to store the walking ability data as associated with a judgment time in the judgment table. In this instance, the information reporting unit is configured to read out a recent one of the walking ability data from the judgment table and report the same. Thus, the user can be informed of most recent data with regard to one's walking ability of routine activity.

Preferably, the diagnosis section is configured to analyze a leg strength for each of the left and right user's legs, to determine a representative value of the leg strengths of the left and right user's legs as well as a leg balance ratio between the left leg strength and the right leg strength so as to judge walking ability as a combination of said representative value and the leg balance ratio, and to store the walking ability as associated with a judgment time in the judgment table. With this arrangement, the user can acknowledge the left and right leg strengths as well as a difference therebetween with regard to one's routine walking activity.

Further, the present system is preferred to include verified information capturing means for obtaining physical characteristic data of the users, and a user table for storing characteristic data with regard to a plurality of the users. The user table is configured to store user codes and physical judgment data specifying physical characteristics of the users. The judgment table is configured to store the user code. The server includes a user identification section which is configured to select the user code in match with the physical judgment data based upon the physical characteristic data obtained at the verified information capturing means, and provide thus selected user code to the diagnosis section. The diagnosis section is configured to store the walking ability data in association with the user code in the judgment table. The information reporting unit is equipped with user selection means for selecting the user code from within the user table, and is configured to read out the walking ability data in match with the selected user code from the judgment table, and to display the same. With the addition of such verification scheme, it is possible that the plural users can use the system to see their own walking abilities.

The sensor unit may include a plurality of floor-mounted load sensors adapted to be mounted on a floor of the premises. In this instance, the diagnosis section can define the leg strength by one of the followings:

a) a longer one of left and right floor-contact times (TR and TL) measured respectively for the left and right user's legs to start from the touching of the foot with the floor and end with the leaving of the foot from the floor, b) a greater one of left and right loads (FR and FL) acting respectively from the left and right user's feet to the floor, c) a greater one of left and right foot steps respectively of the left and right user's feet; and d) a less one of left and right offset distances measured respectively of the left and right user's feet from a travel path of a user's weight center to laterally spaced touching points where the left and right feet touch the floor.

Further, the diagnosis section is configured to define the leg balance ratio by one of the followings:

e) a ratio between the left and right floor-contact times, f) a ratio between the left and right loads, g) a ratio between the left and right foot steps, h) a ratio between the left and right offset distances, and i) a ratio between the left and right toe angles.

Further, the sensor unit may includes a plurality of floor-mounted load sensors adapted to be mounted on a floor of the premises, and a plurality of handrail-mounted load sensors adapted to be disposed along a length of a handrail provided for a stairway or corridor of the premises. In this instance, the diagnosis section is configured to measure a hand load acting on the handrail and a foot load acting on the floor for each of the left and right feet based upon floor signals generated from the floor-mounted load sensors and handrail signals generated from the handrail-mounted load sensors as the user moves along the stairway or the floor, and to obtain a load ratio between the hand load and the foot load for each of the left and right feet. The diagnosis section is configured to determine the representative value as a smaller one of the load ratios, and define the leg balance ratio as a ratio between the left foot load and the right foot load. Thus, it is possible to give the walking ability of the user moving along the stairway.

Preferably, the server includes an exercise projecting section configured to prepare an exercise project corresponding to the determined walking ability data, and to write thus prepared exercise project in the judgment table, and further includes an exercise machine by which the user practices the exercise project. The exercise machine is provided with a movable member which applies an external force to the user. In this instance, the information providing section is configured to transmit the exercise project to the exercise machine by way of the communication network. The exercise machine includes a control section which controls the movable member in order to give an exercise movement to the user in accordance with the exercise project. With this arrangement, the user is enabled to execute an optimum exercise project for improving one's routine walking activity.

In this connection, the exercise machine includes user selection means for selection of the user code from within the user table, and is configured to read out the exercise project relating the selected user code, and provide the exercise project to the control section. Accordingly, even when the system is utilized by plural users, each user can make an exercise in match with an optimum exercise project reflecting one's own walking ability.

Particularly, the exercise machine is incorporated together with the information reporting unit into a unitary structure, whereby the user can practice the exercise machine in well acknowledgement of one's own walking ability.

Furthermore, the exercise machine is preferred to cause the movable member to give a passive exercise movement of stretching muscles of the user according to the exercise project. Thus, the user can be forced to practice the exercise rather unconsciously.

One example of the exercise machine may be composed of a seat for bearing the user's buttocks and a footrest for the user's foot. The seat is controlled to vary its position in accordance with the exercise project, while the footrest is configured to keep the user's knee joint at a constant angle irrespective of the position of the seat. With this result, the user can strengthen the legs free from considerable load acting on the one's knee joints.

Further, the exercise machine is preferred to include a base and a drive mechanism for moving the seat above the base, and the footrest is composed of a pair of left and right foot plates spaced in a lateral direction of the base. The drive mechanism is configured to alternately make a left leg movement of reciprocating the seat between a neutral position and a position close to the left foot plate within a vertical plane including the seat in the neutral position and the left foot plate, and a right leg movement of reciprocating the seat between the neutral position and a position close to the right foot plate within a vertical plane including the seat in the neutral position and the right foot plate. In this instance, the control section is configured to vary a shifting amount of the seat relative to the foot plate in each of the left and right leg movements, while the control section is configured to determine shifting amounts of the seat respectively in the left and right leg movements in accordance with the leg strength and the leg balance ratio defined by the exercise project. With the use of thus configured exercise machine, the user suffering from unbalanced leg strength can be given a suitable exercise load for improving the walking ability as well as curing the unbalances legs.

Further, it is preferred that the drive mechanism includes a height adjusting means for adjusting a height of the sear from the base, a shift-amount adjusting means for adjusting the shifting amount for each of the left and right leg movements, a cycle adjusting means for varying a reciprocation cycle of each of the left and right leg movements, and a timer for adjusting a driving time period for driving the seat. In this instance, the control section is configured to control at least one of the height adjusting means, the shift-amount adjusting means, the cycle adjusting means, and the timer in accordance with the leg strength and the leg balance ratio provided by the exercise project, thereby giving an exercise load optimum for improvement of the user's walking ability.

Further, the user table is preferred to store height data of the users. In this instance, the diagnosis section is configured to read out the height data from the user table based upon the user code and add the height data to the exercise project. The control section is configured to vary the height of the seat based upon the height data, thereby enabling to set a suitable knee angle in match with the user's height.

The system is preferred to have an exercise control table configured to store exercise control information including parameters in association with the walking ability data specified by the exercise project, the parameters being used in the height adjusting means, the shift-amount adjusting means, the cycle adjusting means, and the timer of the exercise machine. In this instance, the control section of the exercise machine is configured to control the movable member in accordance with the exercise control information corresponding to the walking ability data derived from the judgment table, thereby giving a suitable exercise load to the user.

The exercise control table may be located in a data server connected to the server through the communication network, or in the server.

The sensor unit utilized in the present system may be a camera for taking an image of the user in walking. In this instance, the diagnosis section is configured to determine the walking ability on a basis of the image of the user in walking.

Further, the present system may include an exercise machine table which stores different kinds of the exercise machines and exercise performances expected respectively to the exercise machines. In this instance, the diagnosis section is configured to obtain, from the exercise machine table, an exercise machine code optimum for the determined walking ability data, and transmit the exercise machine code to the information reporting unit which responds to report information about the exercise machine corresponding to thus transmitted exercise machine code. This arrangement enables to select a suitable one of the exercised machines suitable for the user's walking ability.

BRIEF DESCRIPTION OF THE DRAWINGS

FIG. 2 is a schematic view illustrating the use of the system;

FIG. 3 is a schematic view illustrating a manner of using an exercise machine employed in the system;

FIG. 4 is a schematic view illustrating a manner of using another exercise machine employed in the system;

FIG. 14 is a perspective view of a second exercise machine employed in the system;

FIG. 15 is a schematic view illustrating an operation of the second exercise machine;

FIG. 16 is a schematic view illustrating an operation of the second exercise machine;

FIG. 17 is a schematic view illustrating an operation of the second exercise machine;

FIG. 18 is a schematic view illustrating an operation of the second exercise machine;

FIG. 19 is an explanatory view illustrating measurement data prepared by the system;

FIG. 20 is an explanatory view illustrating a user table prepared by the system;

FIG. 21 is an explanatory view illustrating a judgment table prepared by the system;

FIG. 22 is an explanatory view illustrating a user judgment data history view prepared by the system;

FIG. 23 is an explanatory view illustrating a leg strength conversion table referred in the system;

FIG. 24 is an explanatory view illustrating exercise project controlling parameters prepared in the system;

FIG. 25 is an explanatory view illustrating an exercise machine table referred in the system;

FIG. 26 is an explanatory view illustrating an exercise control table referred in the system;

BEST MODE FOR CARRYING OUT THE INVENTION

Figure 1:
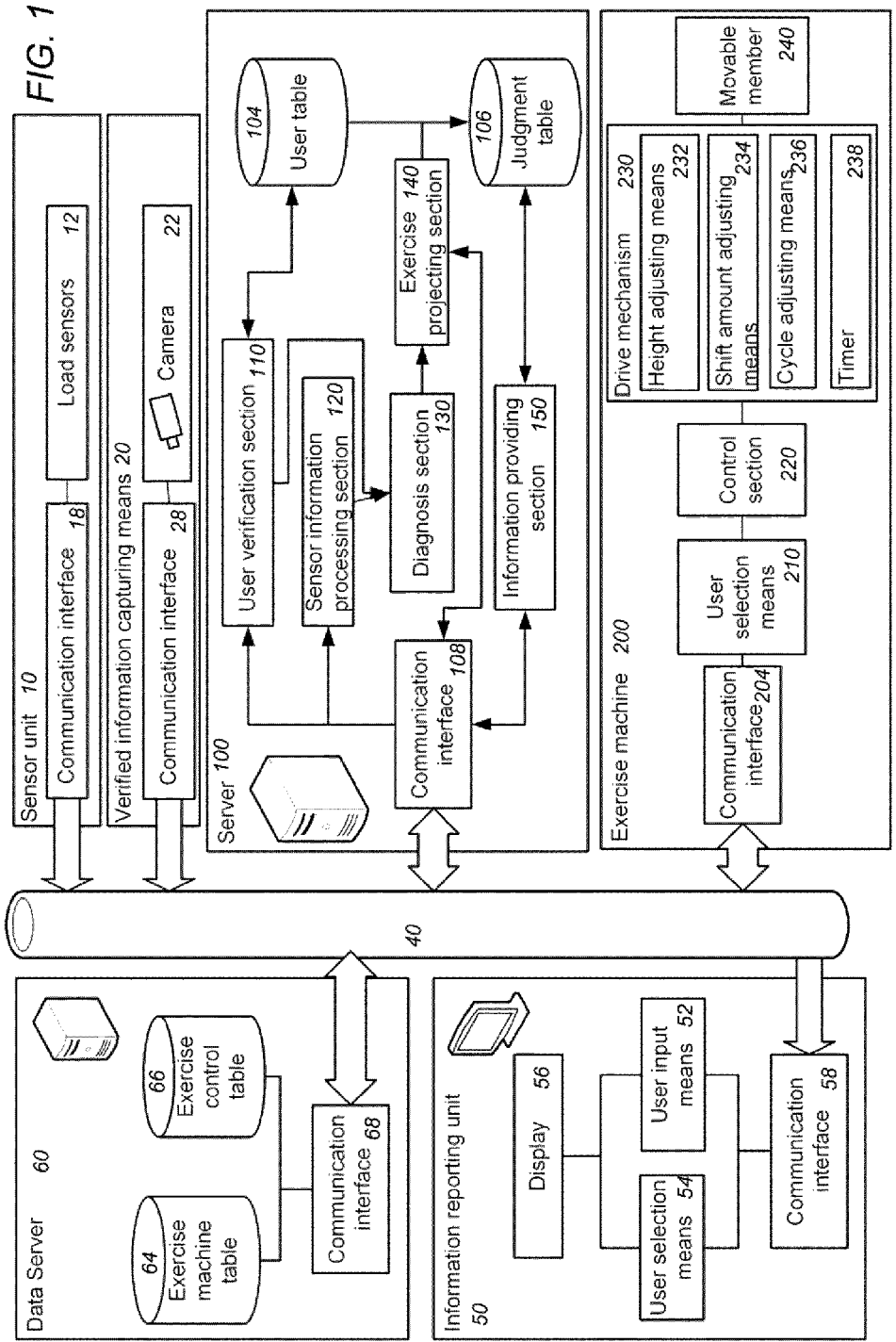
FIG. 1 is a block diagram illustrating a walking ability diagnosis system in accordance with one embodiment of the present invention.

Referring to drawings, there is shown a walking ability diagnosis system in accordance with one embodiment of the present invention. As shown in FIG. 2, the system is adapted to be installed in a premises such as a residential building or clinic for analyzing a user's walking ability based on routine walking behavior in the premises in order to provide a diagnosis report to the user, and provide an exercise project as necessary, for promoting the user to practice the exercise project. As shown in FIG. 1, the system has a basic configuration composed of a sensor unit 10 which is mounted on a floor of a bedroom, kitchen, corridor or suitable location for monitoring the walking behavior of the user, a server 100 connected to receive output of the sensor unit 10 by way of a communication network 40 provided in the premises, an information reporting unit 50 which reports walking ability data determined by a diagnosis section realized in the server 100, and an exercise machines 200 and 300. The information reporting unit 50 and the exercise machine 200 and 300 are connected to the server 100 via the network 40. As shown in FIGS. 3 and 4, different kinds of exercise machines 200 and 300 are employed and installed on a suitable site of the premises, for example, a washroom. The system further includes a verified information capturing means 20 for taking personal identification information of the users. The information capturing means 20 is composed of a camera 22 taking a face image of the user, and a communication interface 28 to analyze the face image for identification of the user, enabling the diagnosis of the walking ability for each of the plural users, as will be discussed later.

Figure 5:
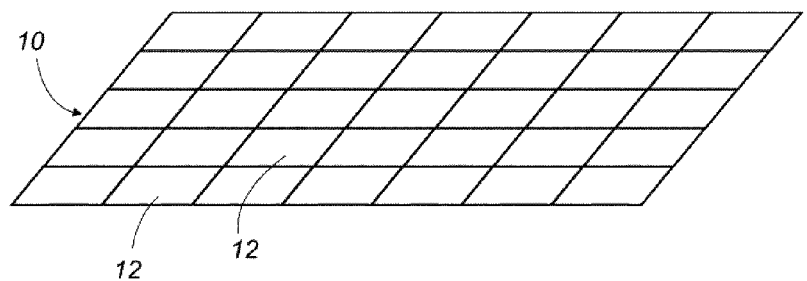
FIG. 5 is a schematic view illustrating an installation of a sensor unit employed in the system.

As shown in FIG. 5, the sensor unit 10 is composed of a plurality of floor-load sensors 12 and a communication interface 18 for transmitting load data as a walking signal to the server 100 via the interface 18, the load data being data of a user's load applied to the floor and monitored by the load sensors 12 arranged in a matrix on the floor while the user is walking on the floor.

The server 100 is composed of a micro-processing means with a CPU, a hard disk, a memory, communication interface 108 to constitute a user verification section 110, a sensor information processing section 120, a diagnosis section 130, an exercise projecting section 140, an information providing section 150, a user table 104, and a judgment table 106, as shown in FIG. 1.

The information reporting unit 50 is composed of a micro-processing means with a CPU, a memory, an input interface, a communication interface 58, and a display 56 to constitute a user input means 52 and a user selection means 54 both accessible by the user.

The user table 104 realized in the server 100 has a data structure of FIG. 20 for storing a user code, age, sex, height, and update date, in addition to face judgment data obtained by analysis of the face image taken by the camera 22 at the user identification section 110. That is, when the face image taken by the camera 22 is found to have a characteristic feature different from that of the face judgment data already stored in the user table 104, the user identification section 110 responds to give a face judgment data specifying the characteristic feature of the face image, and prepare a new record of the face judgment data with a new user code, and transmit an input demand signal to the user input means 52 of the information reporting unit 50, prompting the user to enter user information (name, age, sex, and height) related to the user code. In response to the input demand signal, the user input means 52 urges the user to enter the necessary user information and transmit the input user information to the user identification section 110 so that the user identification section 110 completes the new user data and transmits the corresponding user code to the diagnosis section 130. Thereafter, the system goes into an analysis mode in which the diagnosis section 130 analyzes the walking behavior of the user and associates the analysis result with the user code for storing the data in the judgment table 106. When, on the other hand, the face image taken by the camera is found to have the characteristic feature matching with one of the face judgment data already stored in the user table 104, the user identification section 110 reads out the corresponding user code and transmit the code to the diagnosis section 130 so that the diagnosis section 130 responds to associate the analysis result with the user code and storing the same in the judgment table.

During the analysis mode, the measurement data in the form of time series data of the walking signal from the load sensors 12 is stored in the sensor information processing section 120 together with a timestamp indicative of a time of obtaining the data, such that the diagnosis section 130 analyzes the time series data to give quantized data of the user's walking ability for storing the data in the judgment table 106.

The diagnosis section 130 operates to analyze the time series data within a predetermined time range for measurement of a leg strength for each of the left and right legs, to determine a representative value of the left and right leg strengths as well as a leg balance ratio which is a ratio between the left and right leg strengths, and to prepare the walking ability data, a combination of the representative value of the leg strength and the leg balance ratio. Then, the diagnosis section 130 stores the walking ability data as associate with the judgment time in the judgment table 106. The representative value is selected from one the followings:
a) a longer one of left and right floor-contact times (TR and TL) measured respectively for the left and right user's legs and starting from the touching of the foot with the floor and ending with the leaving of the foot from the floor,
b) a greater one of left and right loads (FR and FL) acting respectively from the left and right user's feet to the floor,
c) a greater one of left and right foot steps respectively of the left and right user's feet; and
d) a less one of left and right offset distances measured respectively of the left and right user's feet from a travel path of a user's weight center to laterally spaced touching points where the left and right feet touch the floor.

The leg balance ratio is selected from one of the followings:
e) a ratio between the left and right floor-contact times,
f) a ratio between the left and right loads,
g) a ratio between the left and right foot steps,
h) a ratio between the left and right offset distances, and
i) a ratio between the left and right toe angles;

For this purpose, the sensor information processing section 120 stores measured parameters required for the above analysis.

Figure 6:
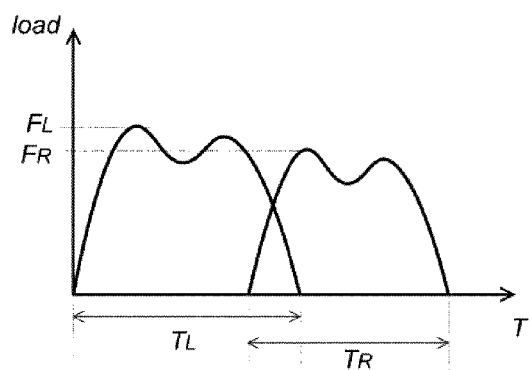
FIG. 6 is a graph illustrating a first criterion of how the system determines walking ability.

Next, an explanation is made to one criterion relied upon for analysis at the diagnosis section 130 with reference to FIG. 6. Generally, a variation in the load applied to the floor during the user's walking results in a waveform of FIG. 6, and it is known that a stronger leg gives rises to a greater load as well as a longer floor-contact than a weaker leg. The waveform of FIG. 6 shows a condition where the load (FL) of the left leg is greater than the load (FR) of the right leg, and the floor-contact time (TL) of the left leg is longer than the floor-contact time (TR) of the right foot, which indicates that the right leg has less leg strength than the left leg. Following explanation is made to the one criterion for judgment of such walking ability on a basis of that the leg strength is defined as the longer one of the left and right floor-contact times (TR and TL) measured starting from the touching of the foot to the floor and ending with the leaving of the foot from the floor, and that the leg balance ratio is defined as a ratio between the left and right floor contact times.

As shown in FIG. 19, the sensor information processing section 120 is configured to store the left-foot floor-contact time (TL) and the right-foot floor contact time (TR). The diagnosis section 130 operates to obtain an average for each of TL and TR from the data measured within a predetermined time range, and to select the longer average of the floor-contact time TL (the left leg or foot, in this instance) as the leg strength, and the ratio between the left and the right foot-contact time (TL/TR) as the leg balance ratio. The leg strength (LS) denotes a level determined by a leg strength conversion table of FIG. 23. The leg balance ratio is set to be always greater than one (1) with the lower value being assigned to the denominator, and represented by percentage. A prefix of (+) is given to the ratio when the left leg strength prevails, while the prefix of (−) is given when the right leg strength prevails. Thus determined leg balance ratio is stored together with the leg strength, the user code, and the judgment time in the judgment table 106 having the data structure as shown in FIG. 21.

Figure 7:
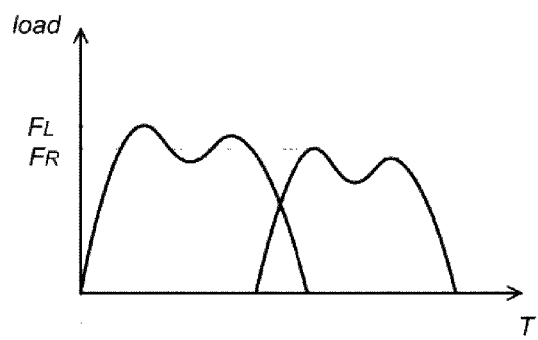
FIG. 7 is a graph illustrating a second criterion of how the system determines walking ability.
Figure 8:
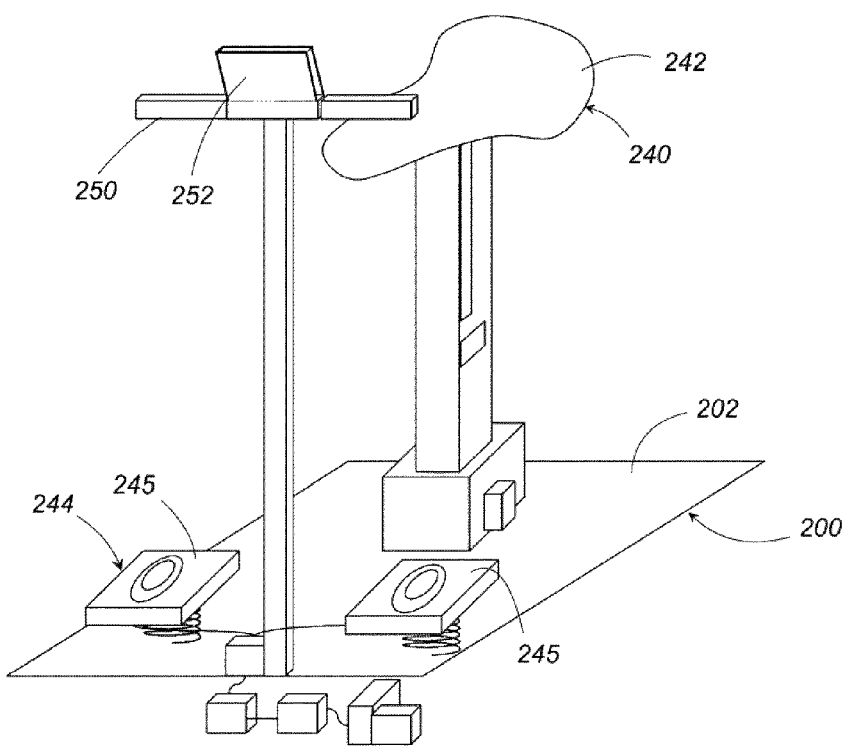
FIG. 8 is a perspective view of a first exercise machine employed in the system.
Figure 9:
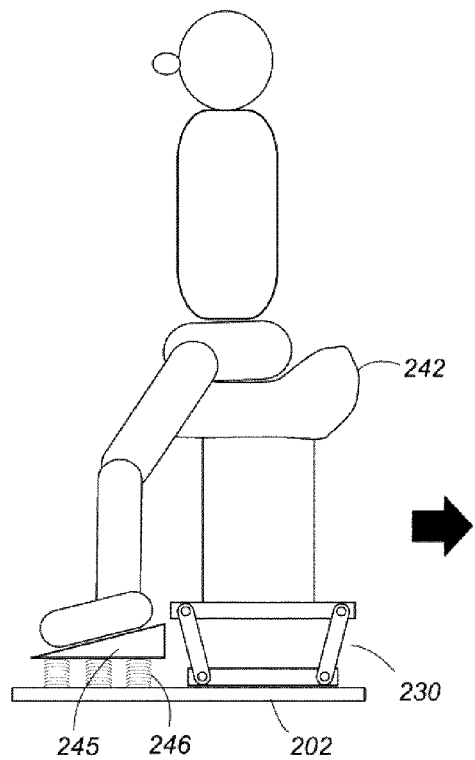
FIG. 9 is a schematic view illustrating an operation of the first exercise machine.
Figure 10:
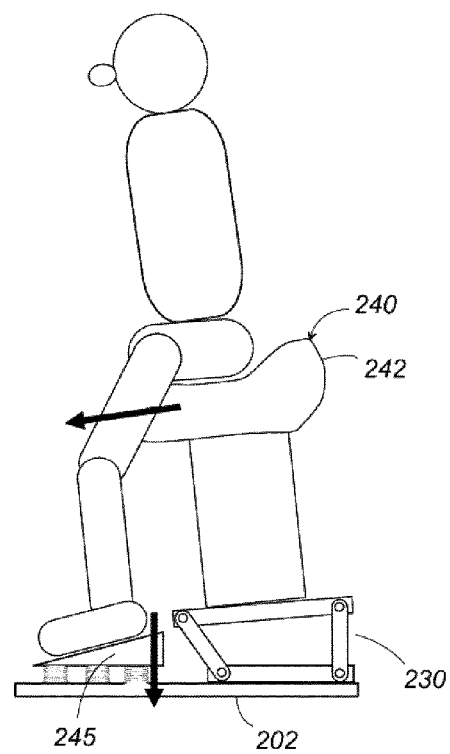
FIG. 10 is a schematic view illustrating an operation of the first exercise machine.
Figure 11:
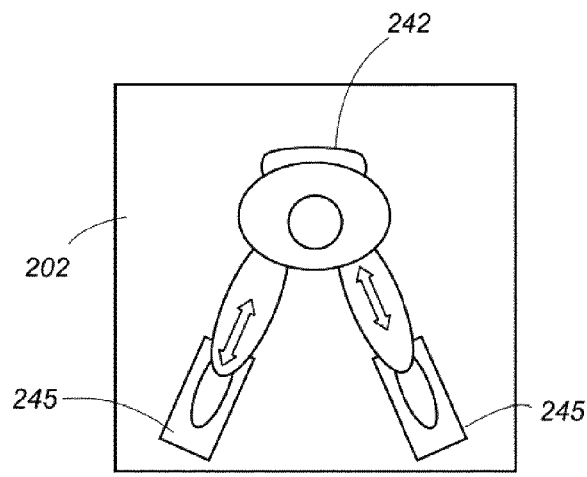
FIG. 11 is a schematic view illustrating an operation of the first exercise machine.

When making the diagnosis of the walking ability based on the load applied from the left and right legs as shown in FIG. 7, the sensor information processing section 120 is configured to store the time series data of the left leg and right leg loads such that the diagnosis section 130 selects a greater averaged one of the loads as the leg strength, and selects the ratio between the left and right leg loads. The leg strength level is determined according to the leg strength conversion table of FIG. 23. The table is stored in the diagnosis section 130 or alternatively in a separately provided data server 60. In the latter instance, the diagnosis section 130 is configured to refer to the leg strength conversion table via the network 40. Other criteria for analysis of the walking ability will be discussed later.

The information providing section 150 in the server 100 functions to transmit the walking ability data determined at the diagnosis section 130 to the information reporting unit 50 and the exercise machine 200. The information reporting unit 50 has the user selection means 54 which transmits the selected user code to the information providing section 150. The information providing section 150 reads out from the judgment table 106 the most recent data corresponding to the user code, and presents the same on the display 56. A displayed content includes an exercise project for improvement of the user's walking ability, in addition to the leg strength and the leg balance ratio. The exercise project is prepared at the exercise projecting section 140 in the server 100, and designates the kind of the exercise machine and a prescription of the exercise. The information reporting unit 50 is configured to read out history data relating to the designated user from the judgment table 106, and present the same on the display 56 in a format as shown in FIG. 22.

In order to improve the walking ability based on the leg strength and the leg balance ratio determined at the diagnosis section 130, the exercise projecting section 140 reads out the user's physical characteristics (height, age, and sex) from the user table, prepares data including the exercise project made in consideration of these parameters, and the exercise machine effective for practicing the exercise project, and store thus prepared data in the judgment table 106.

The exercise machine table 64 in the data server 60 holds data indicating a kind of the exercise machine available in the system as well as its performance. The exercise projecting section 140 reads out the data having a data structure of FIG. 25 from the exercise machine table 64 by way of the network 40 and a communication interface 68 so as to prepare the exercise project. The data server 60 also stores exercise control table 66 having a data structure of FIG. 26 and records for different kinds of the exercise machines. Each of the exercise machines 200 is configured to read out various parameters for execution of the exercise project from the exercise control table 66.

Figure 12:
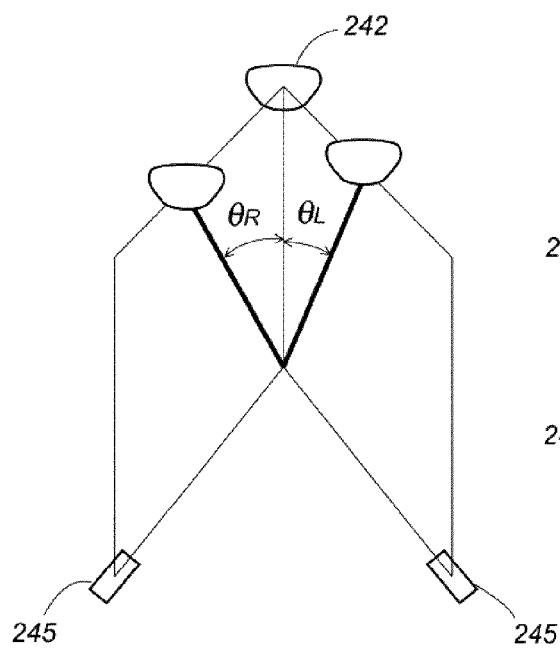
FIG. 12 is a schematic view illustrating an operation of the first exercise machine.
Figure 13:
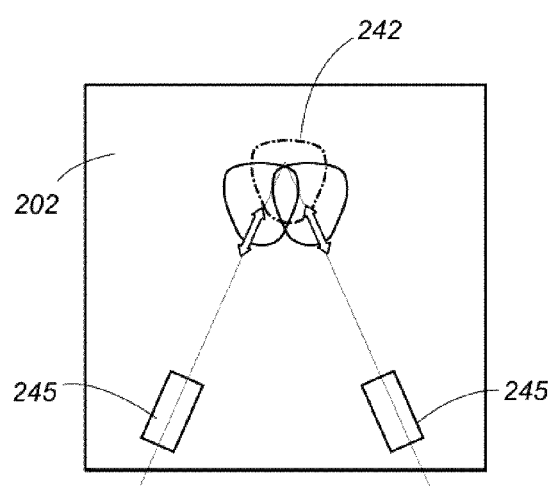
FIG. 13 is a schematic view illustrating an operation of the first exercise machine.

The exercise control table 66 shown in FIG. 26 is provided for control of the first exercise machine 200 shown in FIGS. 8 to 13. Now, an explanation is made as to the operation of this exercise machine 200. The exercise machine 200 includes a communication interface 204 and a movable member 240 which is mounted on a base 202 to give an exercise movement of developing a passive muscle stretching on the side of the user based upon the exercise project transmitted from the server 100 via the network 40. The movable member 240 is composed of a seat 242 bearing the buttocks of the user and a footrest 244 supporting the user's feet. The seat 242 is controlled to vary its position according to the exercise project, while the footrest 244 is configured to keep the user's knee joints at a constant angle irrespective of the varying position of the seat 242. The seat 242 is supported to the base 202 by way of a drive mechanism 230, and is driven to apply the load alternately to the left and right fomora. The footrest 244 is composed of left and right foot plates 245 which are spaced in a lateral direction of the base 202 and floatingly supported to the base 202 by means of respective springs 246. The drive mechanism 230 is configured to alternately make a left leg movement of reciprocating the seat 242 between a neutral position and a position close to left foot plate 245 within a vertical plane including the seat in the neutral position and the left foot plate, and a right leg movement of reciprocating the seat between the neutral position and a position close to the right foot plate within a vertical plane including the seat in the neutral position and the right foot plate. That is, the seat 242 is driven to reciprocate from its neutral position in a direction alternately towards the left and right foot plates 245 within a predetermined angular range ($\theta R$ and $\theta L$), as shown in FIG. 12, thereby generating the exercise movement for improving the muscle strength of the left and right legs. The angular range ($\theta R$ and $\theta L$) is defined in terms of the leg strength and the leg balance ratio determined at the diagnosis section 130, as will be discussed later. Although such leg exercise is accompanied with the movement of the whole legs, each of the foot plates 245 is permitted to move vertically with the user's foot supported thereon under an action of the springs 246, thereby keeping the knee joints at a predetermined angle.

The seat 242 is configured to vary its height from the base by means of the drive mechanism 230, and is set to have the height for adjusting a bending angle of the knee joint at the predetermined angle in consideration of the user's height. The drive mechanism 230 includes a height adjusting means 232 for the seat height adjustment, a shift-amount adjusting means 234 for adjustment of a lateral movement angle, i.e., the shift amount, a cycle adjusting means 236 for a movement cycle adjustment, and a timer 238 for adjustment of the operation time. These means are controlled by a control section 220 to give a suitable movement in match with the exercise project. The exercise machine 200 is further provided with a user selection means 210 which functions to read out the exercise project assigned to the selected user from the server 100 for execution. Entry at the user selection means 210 is made by use of a touch-screen (not seen) in a central panel 252 on a handle 250 of the exercise machine 200, or the like input means. The selected exercise project is presented on the panel 252.

Next, an explanation is made as to a control of the exercise machine 200. The exercise project given from the judgment table 106 includes, as shown in FIG. 24, control parameters such as the leg strength, a reference leg (L/R) indicative of the left or right leg, the leg balance ratio, height, BMI, and sex. BMI (body mass index) is calculated from the user's height, and a user's weight estimated based upon the load given from the load sensors. Upon reading of the exercise project, the control section 210 refers to the exercise control table 66 so as to obtain parameters of the knee angle (°), movement angle range ($\theta$), movement cycle (second), and exercise time (second). At this time, a correction can be made dependent upon the leg balance ratio so as to enhance one of the movement angles, i.e., on the side of the leg determined to be weaker than the other leg. For example, the movement angle obtained from the exercise control table 66 is multiplied by the leg balance ratio and is given to the weaker leg. In addition to or instead of such correction, it is possible to correct the movement cycle of the weaker leg to a greater value in view of the leg balance ratio. Further, the knee angle, the movement angle range, or movement cycle can be corrected based upon the information as to the sex, height, and BMI included in the exercise project. With this control, the exercise machine enables the user to successfully practice the exercise project assigned thereto, thereby promoting the walking ability.

FIGS. 14 to 18 illustrate the second exercise machine 300 available in the present system. The exercise machine 300 is intended to give an exercise to user in standing posture, and includes the movable part defined by a pair of left and right movable foot plates 345. Each of the foot plates 345 is driven by a drive means (not shown) to effect a movement with respect to x-, y-, and z-axis of FIG. 14, alone or in combination. The movement includes a translation within x-y coordinate as shown in FIG. 15, a rotation about x-axis as shown in FIG. 16, a rotation about y-axis as shown in FIG. 17, and a rotation about z-axis as shown in FIG. 18. Likewise the first exercise machine 200, the exercise machine 300 is also equipped with the communication interface, the control section, and the user selection means so as to reciprocate the left and right foot plates respectively within predetermined range and at the predetermined cycles according to the exercise project transmitted from the server 100, thereby imparting a suitable exercise for improvement of the walking ability. The user selection means is formed at a panel 352 which is disposed above the base 302 and is equipped with a display 354 for presentation of the exercise project.

Although the above embodiment illustrates the example of using two kinds of the exercise machine, the other kinds of the exercise machines are equally available in the system of the present invention.

Figures 27, 28:
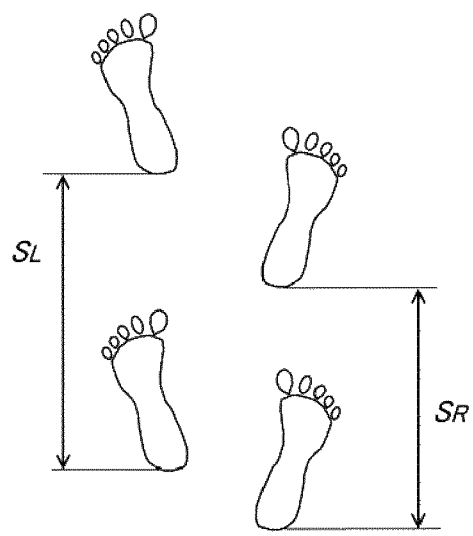
FIG. 27 is an explanatory view illustrating a third criterion of how the system determines walking ability.
FIG. 28 is an explanatory view illustrating measurement data relied upon by the above criterion.

Next, an explanation is made as to another criterion relied upon for analyzing the walking ability at the diagnosis section 130. FIG. 27 illustrate the criterion in which the foot steps SL and SR for the left and right feet are utilized to determine the leg strength and the leg balance ratio. To this end, the sensor unit 10 includes a plurality of pressure sensors for measurement of a pressure distribution with regard to the pressure given from the user to the floor. Each pressure sensor transmits a walking signal indicative of a footprint for each of the left and right feet to the server 100. The sensor information processing section 120 collects the time series data of foot steps (SL and SR) respectively of the left and right feet obtained from the waling signal, as shown in FIG. 28. The diagnosis section 130 obtains the average of each of the left and right foot steps so as to define the representative value of the leg strength by the greater one of the averages, and define the leg balance ration by a ratio between the averages. Then, the diagnosis section 130 refers to the leg strength conversion table and reads the level of the leg strength corresponding to one of the left and right foot steps selected as the leg strength, and stores the level as the leg strength in the judgment table 106 together with the leg balance ratio and the other data. When there is difference of the leg strength between the left and right legs due to a leg disorder, it is known that the weaker leg experiences the less foot step than the stronger leg. In view of this, the present system anticipates that the stronger leg is well representative of the user's normal leg strength, and prepares the information as well as the exercise project for improving the muscle strength of the weaker leg in match with the stronger leg.

Figures 29, 30:
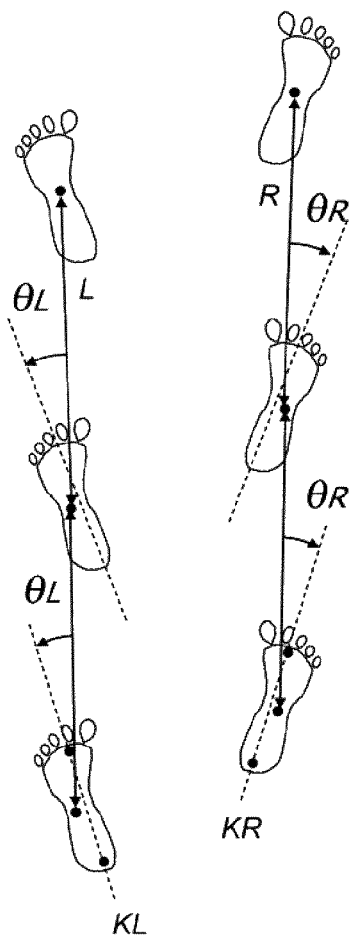
FIG. 29 is an explanatory view illustrating a fourth criterion of how the system determines walking ability.
FIG. 30 is an explanatory view illustrating measurement data relied upon by the above criterion.

FIGS. 29 and 30 illustrate a further criterion for analysis of the walking ability. The criterion relies on the sensor unit 10 composed of a plurality of the pressure sensors to obtain the leg strength in terms of pressure values monitored by the pressure sensors, and define the leg balance ration as a ratio between the tow angles (θL and θR) of the left and right feet. As shown in FIG. 29, when there occurs unbalancing of the leg strength between the left and right leg, it is seen that the tow angle (θR) of the weaker leg (the right leg, in this instance) becomes less than the tow angle (θL) of the other leg. Accordingly, the leg balance ration as well as the stronger leg are determined by comparison of the tow angles of the left and right feet, and the pressure applied from the strong leg to the floor is selected as the representative value of the leg strength. The sensor information processing section 120 collects the time-series data of the tow angles for each of the left and right legs and the pressure values, as shown in FIG. 30, based on the signal output from the pressure sensors. The diagnosis section 130 analyzes the time series data to determine the leg balance ratio which is a ratio between the averages of the tow angles for the left and right feet. The leg strength is obtained from the average of the pressure values measured for the leg of which foot shows a large tow angle than the other. As shown in FIG. 29, the tow angle is defined by an angle at which an inclination line (KL and KR) for each of the left and right feet crosses with a reference line (L and R) for each of the left and right feet. The reference line (L and R) is selected to be traced by a moving weight center calculated from the pressure distribution for each of the left and right feet, while the inclination line (KL and KR) is defined to extend through a touching point of the heel and a kicking point of the tow for each of the left and right feet. The pressure value designating the leg strength is obtained as a sum of the pressures applied on the entire bottom of the foot, and is substantially equal to the load applied from each foot to the floor.

Figures 31, 32:
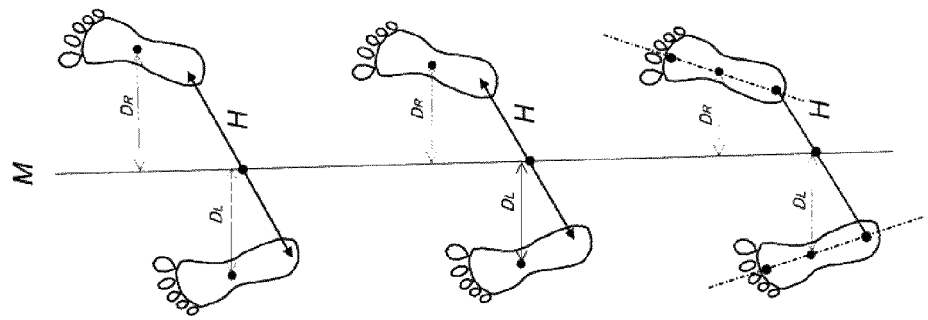
FIG. 31 is an explanatory view illustrating a fifth criterion of how the system determines walking ability.
FIG. 32 is an explanatory view illustrating measurement data relied upon by the above criterion.

FIGS. 31 and 32 illustrate a still further criterion for analysis of the walking ability. The criterion also relies on the sensor unit 10 composed of a plurality of the pressure sensors to measure offset distances (DL and DR) from a travel path of the user's weight center to laterally spaced touching points of the left and right feet on the floor, respectively, in order to define the leg strength in terms of the pressure (load) that one of the left and right feet having less offset distance and define the leg balance ratio as related to a ratio (DL/DR and DR/DL) between the left and right offset distances. As shown in FIG. 31, when there occurs unbalancing between the left and right leg strengths, the weaker leg (the right leg in the illustrated instance) experiences a smaller offset distance from the body weight center towards the lateral direction. Therefore, the analysis is made in terms of the laterally offset distances (DL and DR) from a reference line M traced by the moving body weight center towards the left and right directions in order to determine the leg strength and the leg balance ratio. Also with this analysis, it is made to judge which of the legs is stronger and therefore determine the representative value of the leg strength which is the pressure applied from the stronger leg to the floor. The sensor information processing section 120 collects the time series data of the offset distances (DL and DR) of the left and right feet, and the pressure values, as shown in FIG. 32, from the output signal of the pressure sensors. The diagnosis section 130 analyzes the time series data to obtain the leg balance ratio which is a ratio between the averages of the left and right offset distances. The leg strength is determined as an average of the pressure values measured for the foot showing less offset distance. The reference line M is defined to pass individual centers of lines H each extending between the touching points of the left and right feet. Each of the left and right offset distances (DL and DR) is defined as a distance from the reference line M to the weight center of each foot. Also in this instance, the pressure value designating the leg strength is obtained as a sum of the pressures given to the entire bottom of the foot, and is substantially equal to the load which the feet applies to the floor.

Figures 33, 34:
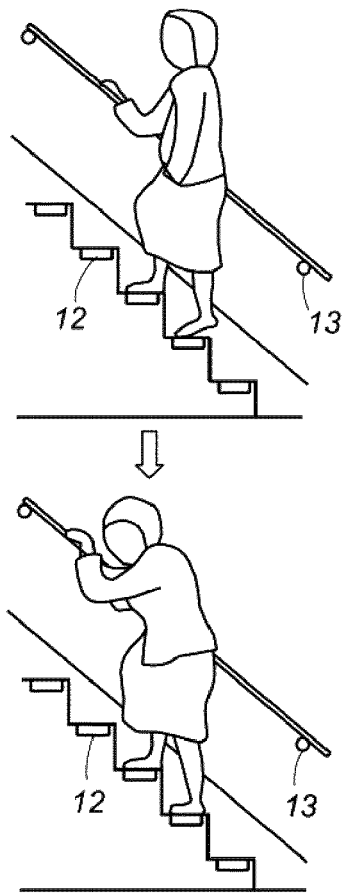
FIG. 33 is a schematic view illustrating a user's walking posture in a case the sensor unit is mounted on the side of a stairway.
FIG. 34 is an explanatory view illustrating measurement data for determination of the walking ability of the user moving up and down the stairway.

FIGS. 33 and 34 illustrate a criterion for analysis of the walking ability of the user walking along the stairway with a handrail. The criterion relies upon the sensor unit 10 having a plurality of load sensors 12 provided respectively at the steps of the stairway, and load sensors 13 provided at the handrail. In addition, a plurality of pressure sensors are arranged along the handrail to detect positional change of the user holding the handrail for providing an output determining whether the user is going up or down. The load sensors are spaced laterally at each step of the stairway in order to detect which one of the left and right legs applies a load to the step when going up and down the stairway. When going up and down the stairway, it is found that the load applied to the handrail will increase as the leg strength becomes weaker, and also that a ratio between the loads applied to the step and the handrail will vary depending upon the difference in the leg strength between the left and right legs. In this instance, the leg strength and the leg balance ratio are defined based upon the above finding. That is, the representative value of the leg strength is defined to be less one of ratios of the handrail load to the floor load (H/F) for the left and right legs, while the leg balance ratio is defined to a ratio between these two ratios for the leg and right legs. In this connection, the sensor information processing section 120 collects, as shown in FIG. 34, time series data of the floor loads applied to the steps of the stairway and the handrail loads applied to the handrail. The diagnosis section 130 analyzes the time series data to obtain an averaged ratio of the handrail loads to the floor loads for each of the left and right legs so as to determine the representative value which is less one of the ratios for the left and right legs, and the leg balance ratio which is the ratio between the averaged ratio of the handrail load to the floor load for the left leg and the averaged ratio of the handrail load to the floor load for the right leg. Based upon thus determined representative value of the leg strength, the leg strength is selected from values which are ranked in accordance with a predetermined relationship like the above mentioned leg strength conversion table.

The criteria disclosed in the above for obtaining the leg strength and the leg balance ratio can be used in suitable combination, and the leg strength determined according to one criterion can be used in combination with the leg balance ratio determined according to different criterion.

Although the above embodiments disclose to obtain the leg balance ratio between the left and right leg strength and provide the exercise project which gives different loads to the left and right legs, the present invention should not be limited to these embodiments and is interpreted to encompass a modification which reports only the determined leg strength or provides an exercise project causing no different load between the left and the right legs.

Further, although the above embodiments disclose the criteria for determination of the user's walking ability with the use of the load sensors or the pressure sensors on the floor, the present invention should be not limited thereto and may use a camera taking a picture of the user in walking as the sensor in order to estimate the walking ability or the exercise ability for reporting the exercise ability or providing an exercise project of improving the exercise ability. In this instance, the sensor unit is provided with a communication interface for transmitting time series data of the images taken by the camera to the server. The server is provided with a sensor output processing section which holds the time series data temporarily such that the diagnosis section of the serve analyzes the time series data through image processing for determination of the walking ability. For instance, the image processing is made to extract angular variations of the ankle joint and the knee joint for determination of the waling ability based upon an index showing the angular variation of at least one of the joints. The index may be, for example, a minimum angle of the ankle joint or an increasing ratio of the angle of the ankle joint starting from the minimum angle (an instant of kicking the foot). Further, it is equally possible to determine knock-kneed or bow legs based upon the image processing and provide the exercise project for curing the leg shape.

The invention claimed is:

1. A walking ability diagnosis system comprising:
a sensor unit installed in a premises and configured to measure walking behavior of a user;
a server connected to said sensor unit by way of a communication network provided in said premises; and
an information reporting unit connected to said server by way of said communication network,
wherein said sensor unit being configured to provide a walking signal indicative of the user's walking behavior, and said server comprises:
a sensor information processing section configured to store time series data of said walking signal transmitted from said sensor unit;
a diagnosis section configured to analyze said time series data to determine the walking ability and generate walking ability data indicative of the walking ability; and
an information providing section configured to transmit said determined walking ability data to said communication network,
said information reporting unit including resorting means for providing the walking ability data determined at said server to said user,
wherein
said server has a judgment table,
said diagnosis section is configured to analyze a leg strength based upon said time series data within a predetermined time range, to determine the same as the walking ability data, and to store said walking ability data as associated with a judgment time in said judgment table, and
said information reporting unit is configured to read out a recent one of said walking ability data from said judgment table and report the same,
wherein
said server includes an exercise projecting section configured to prepare an exercise project corresponding to the determined walking ability data, and to write thus prepared exercise project in said judgment table,
said system further including an exercise machine by which the user practices said exercise project, said exercise machine being provided with a movable member which applies an external force to the user,
said information providing section being configured to transmit said exercise project to said exercise machine by way of said communication network, and
said exercise machine including a control section which is configured to control said movable member in order to give an exercise movement to the user in accordance with the exercise project.

2. A walking ability diagnosis system comprising:
a sensor unit installed in a premises and configured to measure walking behavior of a user;
a server connected to said sensor unit by way of a communication network provided in said premises; and
an information reporting unit connected to said server by way of said communication network,
wherein said sensor unit being configured to provide a walking signal indicative of the user's walking behavior, and said server comprises:
a sensor information processing section configured to store time series data of said walking signal transmitted from said sensor unit;
a diagnosis section configured to analyze said time series data to determine the walking ability and generate walking ability data indicative of the walking ability; and
an information providing section configured to transmit said determined walking ability data to said communication network,
said information reporting unit including reporting means for providing the walking ability data determined at said server to said user,
wherein
said server has a judgment table,
said diagnosis section is configured to analyze a leg strength for each of the left and right user's legs based upon said time series data within a predetermined time range, to determine a representative value of the leg strengths of the left and right user's legs as well as a leg balance ratio between the left leg strength and the right leg strength so as to define the walking ability as a combination of said representative value and said leg balance ratio, and to store said walking ability as associated with a judgment time in said judgment table, and
said information reporting unit is configured to read out a recent one of said walking ability data from said judgment table and report the same,
wherein
said server includes an exercise projecting section configured to prepare an exercise project corresponding to the determined walking ability data, and to write thus prepared exercise project in said judgment table,
said system further including an exercise machine by which the user practices said exercise project, said exercise machine being provided with a movable member which applies an external force to the user,
said information providing section being configured to transmit said exercise project to said exercise machine by way of said communication network, and
said exercise machine including a control section which is configured to control said movable member in order to give an exercise movement to the user in accordance with the exercise project.

3. A walking ability diagnosis system as set forth in claim 1, further including:
verified information capturing means configured to obtain physical characteristic data of the users, and a user table configured to store characteristic data with regard to a plurality of the users,
said user table being configured to store user codes and physical judgment data specifying physical characteristics of the users, said judgment table being configured to store said user code, said server including a user identification section configured to select the user code in match with the physical judgment data based upon the physical characteristic data obtained at said verified information capturing means, and provide thus selected user code to said diagnosis section, said diagnosis section being configured to store the walking ability data in association with said user code in said judgment table, said information reporting unit being equipped with user selection means for selecting the user code from within said user table, and being configured to read out the walking ability data in match with the selected user code from said judgment table, and to display the same.

4. A walking ability diagnosis system as set forth in claim 1 or 2, further including:

verified information capturing means configured to obtain physical characteristic data of the user, and a user table configured to store characteristic data with regard to a plurality of the users, said user table being configured to store user codes and physical judgment data specifying physical characteristics of the users, said judgment table being configured to store said user code, said server including a user identification section configured to select the user code in match with the physical judgment data based upon the physical characteristic data obtained at said verified information capturing means, and provide thus selected user code to said diagnosis section, said diagnosis section being configured to store the determined walking ability data in association with said user code in said judgment table, said exercise machine being equipped with user selection means for selecting the user code from within said user table, and being configured to read out the exercise project relating the selected user code, and provide the exercise project to said control section.

5. A walking ability diagnosis system as set forth in claim 4, wherein said exercise machine and said information reporting unit is incorporated into a unitary structure.

6. A walking ability diagnosis system as set forth in claim 4, wherein said exercise machine is configure to cause said movable member to give a passive exercise movement of stretching muscles of the user according to said exercise project.

7. A walking ability diagnosis system as set forth in claim 6, wherein said movable member is composed of a seat for hearing the user's buttocks and a footrest for the user's foot, said seat being controlled to vary its position in accordance with said exercise project, and said footrest being configured to keep the user's knee joint at a constant angle irrespective of the position of said seat.

8. A walking ability diagnosis system as set forth in claim 7, wherein said exercise machine comprises a base and a drive mechanism for moving said seat above the base, and said footrest is composed of a pair of left and right foot plates spaced in a lateral direction of said base, said drive mechanism being configured to alternately make a left leg movement of reciprocating said seat between a neutral position and a position close to said left foot plate within a vertical plane including the seat in said neutral position and said left foot plate, and a right leg movement of reciprocating said seat between said neutral position and a position close to said right foot plate within a vertical plane including the seat in said neutral position and said right foot plate, said control section being configured to vary a shifting amount of said seat relative to said foot plate in each of said left and right leg movements, and said control section being configured to determine shifting amounts of said seat respectively in said left and right leg movements in accordance with said leg strength and said leg balance ratio defined by said exercise project.

9. A walking ability diagnosis system as set forth in claim 8, wherein said diagnosis section is configured to define said leg strength by one of the followings:

a) a longer one of left and right floor-contact times (TR and TL) measured respectively for the left and right user's legs and starting from the touching of the foot with the floor and ending with the leaving of the foot from the floor, b) a greater one of left and right loads (FR and FL) acting respectively from the left and right user's feet to the floor, c) a greater one of left and right foot steps respectively of the left and right user's feet;

d) a less one of left and right offset distances measured respectively of the left and right user's feet from a travel path of a user's weight center to laterally spaced touching points where the left and right feet touch the floor, and said diagnosis section is configured to define said leg balance ratio by one of the followings:

e) a ratio between the left and right floor-contact times, f) a ratio between the left and right loads, g) a ratio between the left and right foot steps, h) a ratio between the left and right offset distances, and i) a ratio between the left and right toe angles;

wherein said diagnosis section is configured to store the defined leg strength and the leg balance ratio in said judgment table.

10. A walking ability diagnosis system as set forth in claim 8, wherein said sensor unit comprises a plurality of floor-mounted load sensors adapted to be mounted on a floor of said premises, and a plurality of handrail-mounted load sensors adapted to be disposed along a length of a handrail provided for a stairway or corridor of the premises, said diagnosis section being configured to obtain a load ratio based upon floor signals generated from said floor-mounted load sensors and handrail signals generated from said handrail-mounted load sensors as the user moves along the stairway or the floor, to obtain a load ratio between a hand load acting on the handrail and a foot load acting on the floor for each of the left and right feet, said diagnosis section being configured to determine the representative value as a smaller one of the load ratios, and determine the leg balance ratio as a ratio between the load ratio for the left foot and that for the right foot.

11. A walking ability diagnosis system as set forth in claim 8, wherein said drive mechanism comprises:

a height adjusting means for adjusting a height of the seat from said base;

a shift-amount adjusting means for adjusting said shifting amount for each of the left and right leg movements;

a cycle adjusting means for varying a reciprocation cycle of each of the left and right leg movements; and a timer for adjusting a driving time period for driving said seat, said control section being configured to control at least one of said height adjusting means, said shift-amount adjusting means, said cycle adjusting means, and said timer in accordance with said leg strength and said leg balance ratio provided by said exercise project.

12. A walking ability diagnosis system as set forth in claim 8, wherein said drive mechanism is configured to adjust a height of said seat from said base, said user table being configured to store height data of the users, said diagnosis section being configured to read out the height data from said user table based upon the user code and add the height data to said exercise project, and said control section being configured to vary the height of said seat based upon the height data.

13. A walking ability diagnosis system as set forth in claim 11, further including:

an exercise control table configured to store exercise control information including parameters in association with the walking ability data specified by said exercise project, said parameters being used in said height adjusting means, said shift-amount adjusting means, said cycle adjusting means, and said tinier of said exercise machine, and said control section of the exercise machine being configured to control said movable member in accordance with the exercise control information corresponding to the walking ability data derived from said judgment table.

14. A walking ability diagnosis system as set forth in claim 13, wherein said exercise control table is located in a data server connected to said server through said communication network.

15. A walking ability diagnosis system as set forth in claim 13, wherein said exercise control table is located in said server.

16. A walking ability diagnosis system as set forth in claim 1 or 2, wherein said sensor unit comprises a camera which takes an image of the user in walking, said diagnosis section being configured to determine the walking ability on a basis of the image of the user in walking.

17. A walking ability diagnosis system as set forth in claim 1 or 2, further including:

an exercise machine table configured to store different kinds of the exercise machines and exercise performances expected respectively to said exercise machines, said diagnosis section being configured to obtain, from said exercise machine table, an exercise machine code optimum for the determined walking ability data, and transmit the exercise machine code to said information reporting unit, and said information reporting unit being configured to report information about the exercise machine corresponding to thus transmitted exercise machine code.

18. A walking ability diagnosis system as set forth in claim 2 or 3, wherein said sensor unit comprises a plurality of floor-mounted load sensors adapted to be mounted on a floor of said premises, and said diagnosis section is configured to analyze the walking signal from the floor-mounted load sensors to obtain a floor-contact time (TR and TL) for each of the left and right user's feet, said floor-contact time starting from the touching of the foot with the floor and ending with the leaving of the foot from the floor, said diagnosis section being configured to determine said leg strength as a longer one of the floor-contact times, and determine said leg balance ratio as a ratio of one of said floor-contact times to the other.

19. A walking ability diagnosis system as set forth in claim 2 or 3, wherein said sensor unit comprises a plurality of floor-mounted load sensors adapted to be mounted on a floor of said premises, and said diagnosis section is configured to analyze the walking signal from the floor-mounted load sensors to obtain a load (FR and FL) acting on the floor from each of the left and right user's feet, determine said leg strength as a greater one of the loads, and determine said leg balance ratio as a ratio of one of the left and right load to the other.

20. A walking ability diagnosis system as set forth in claim 2 or 3, wherein said sensor unit comprises a plurality of floor-mounted load sensors adapted to be mounted on a floor of said premises, and said diagnosis section is configured to analyze the walking signal from the floor-mounted load sensors to obtain a foot step for each of the left and right user's feet, determine said leg strength as a greater one of the foot steps, and determine said leg balance ratio as a ratio of one of the right and left foot steps to the other.

21. A walking ability diagnosis system comprising:

a sensor unit installed in a premises and configured to measure walking behavior of a user;

a server connected to said sensor unit by way of a communication network provided in said premises; and an information reporting unit connected to said server by way of said communication network, wherein said sensor unit being configured to provide a walking signal indicative of the user's walking behavior, and said server comprises:

a sensor information processing section configured to store time series data of said walking signal transmitted from said sensor unit;

a diagnosis section configured to analyze said time series data to determine the walking ability and generate walking ability data indicative of the walking ability; and an information providing section configured to transmit said determined walking ability data to said communication network, said information reporting unit including reporting means for providing the walking ability data determined at said server to said user, wherein said server has a judgment table, said diagnosis section is configured to analyze a leg strength for each of the left and right user's legs based upon said time series data within a predetermined time range, to determine a representative value of the lea strengths of the let and right user's legs as well as a leg balance ratio between the left leg strength and the right leg strength so as to define the walking ability as a combination of said representative value and said leg balance ratio, and to store said walking ability as associated with a judgment time in said judgment table, and said information reporting unit is configured to read out a recent one of said walking ability data from said judgment table and report the same, wherein said sensor unit comprises a plurality of floor-mounted load sensors adapted to be mounted on a floor of said premises, and a plurality of handrail-mounted load sensors adapted to be disposed along a length of a handrail provided for a stairway or corridor of the premises, said diagnosis section being configured to measure a hand load acting on the handrail and a foot load acting on the floor for each of the left and right feet based upon floor signals generated from said floor-mounted load sensors and handrail signals generated from said handrail-mounted load sensors as the user moves along the stairway or the floor, and to obtain a load ratio between the hand load and the foot load for each of the left and right feet, said diagnosis section being configured to determine the representative value as a smaller one of the load ratios, and define the leg balance ratio as a ratio between the left foot load and the right foot load.

22. A walking ability diagnosis system comprising:

a sensor unit installed in a premises and configured to measure walking behavior of a user;

a server connected to said sensor unit by way of a communication network provided in said premises; and an information reporting unit connected to said server by way of said communication network, wherein said sensor unit being configured to provide a walking signal indicative of the user's walking behavior, and said server comprises:

a sensor information processing section configured to store time series data of said walking signal transmitted from said sensor unit;

a diagnosis section configured to analyze said time series data to determine the walking ability and generate walking ability data indicative of the walking ability; and an information providing section configured to transmit said determined walking ability data to said communication network, said information reporting unit including reporting means for providing the walking ability data determined at said server to said user, wherein said server has a judgment table, said diagnosis section is configured to analyze a leg strength based upon said time series data within a predetermined time range, to determine the same as the walking ability data, and to store said walking ability data as associated with a judgment time in said judgment table, and said information reporting unit is configured to read out a recent one of said walking ability data from said judgment table and report the same, wherein said walking ability diagnosis system further includes:

verified information capturing means configured to obtain physical characteristic data of the users, and a user table configured to store characteristic data with regard to a plurality of the users, said user table being configured to store user codes and physical judgment data specifying physical characteristics of the users, said judgment table being configured to store said user code, said server including a user identification section configured to select the user code in match with the physical judgment data based upon the physical characteristic data obtained at said verified information capturing means, and provide thus selected user code to said diagnosis section, said diagnosis section being configured to store the walking ability data in association with said user code in said judgment table, said information reporting unit being equipped with user selection means for selecting the user code from within said user table, and being configured to read out the walking ability data in match with the selected user code from said judgment table, and to display the same, wherein said sensor unit comprises a plurality of floor-mounted load sensors adapted to be mounted on a floor of said premises, and a plurality of handrail-mounted load sensors adapted to be disposed along a length of a handrail provided for a stairway or corridor of the premises, said diagnosis section being configured to measure a hand load acting on the handrail and a foot load acting on the floor for each of the left and right feet based upon floor signals generated from said floor-mounted load sensors and handrail signals generated from said handrail-mounted load sensors as the user moves along the stairway or the floor, and to obtain a load ratio between the hand load and the foot load for each of the left and right feet, said diagnosis section being configured to determine the representative value as a smaller one of the load ratios, and define the leg balance ratio as a ratio between the left foot load and the right foot load.

* * * * *